United States Patent [19]

Dew et al.

[11] Patent Number: 5,409,479
[45] Date of Patent: * Apr. 25, 1995

[54] METHOD FOR CLOSING TISSUE WOUNDS USING RADIATIVE ENERGY BEAMS

[75] Inventors: Douglas K. Dew, Maitland; Long S. Hsu, Orlando; Steven J. Halpern, Oviedo, all of Fla.

[73] Assignee: Premier Laser Systems, Inc., Irvine, Calif.

[ * ] Notice: The portion of the term of this patent subsequent to Aug. 8, 2006 has been disclaimed.

[21] Appl. No.: 934,167

[22] Filed: Aug. 24, 1992

Related U.S. Application Data

[60] Continuation-in-part of Ser. No. 639,025, Jan. 9, 1991, Pat. No. 5,140,984, which is a continuation of Ser. No. 380,622, Jul. 14, 1989, Pat. No. 5,002,051, which is a division of Ser. No. 62,861, Apr. 13, 1987, Pat. No. 4,854,320, which is a continuation-in-part of Ser. No. 539,527, Oct. 6, 1983, Pat. No. 4,672,969.

[51] Int. Cl.⁶ .......................... A61N 5/06; A61B 17/36
[52] U.S. Cl. ................................. 606/9; 606/3; 606/11; 606/8
[58] Field of Search ............. 602/2, 3, 10, 11, 15, 602/16, 17; 128/395

[56] References Cited
U.S. PATENT DOCUMENTS

| | | | |
|---|---|---|---|
| 4,672,969 | 6/1987 | Dew | 606/8 |
| 4,854,320 | 8/1989 | Dew et al. | 606/9 |
| 5,002,051 | 3/1991 | Dew et al. | 606/3 |
| 5,140,984 | 8/1992 | Dew et al. | 606/2 |

FOREIGN PATENT DOCUMENTS
8501445 4/1985 WIPO .................... 606/17

Primary Examiner—Stephen C. Pellegrino
Assistant Examiner—Sonya C. Harris
Attorney, Agent, or Firm—Steven C. Stewart; James H. Beusse

[57] ABSTRACT

The method and apparatus of the invention use a beam of laser emitted optical energy to effect wound closure and reconstruction of biological tissue. In response to input as to tissue type and thickness, a computer determines the output power, exposure time and spot diameter of the emitted beam to control the application of optical energy to produce thermal heating of biological tissue. The tissue is heated to a degree suitable for denaturing the tissue proteins such that the collagenous elements of the tissue form a "biological glue" to seal immediately and/or to reconstruct the tissue being heated without any injurious tissue shrinkage. In a given embodiment, the computer directly controls output power of the laser by regulating the laser's input current, and limits exposure time by deactivating a shutter mechanism when the predetermined time is reached. Beam diameter is manually set in response to a displayed value with a scale that controls the working distance between the end of a fiber optic beam guide and the tissue site.

16 Claims, 8 Drawing Sheets

METHOD FOR CLOSING TISSUE WOUNDS USING RADIATIVE ENERGY BEAMS

This application is a CIP of Ser. No. 07/639,025, Jan. 09, 1991, U.S. Pat. No. 5,140,984 which is a continuation of Ser. No. 07/380,622, Jul. 14, 1989, U.S. Pat. No. 5,002,051 which is a division of Ser. No. 07/062,861, Apr. 13, 1987, U.S. Pat. No. 4,854,320 which is a continuation-in-part of Ser. No. 07/539,527, Oct. 6, 1983, U.S. Pat. No. 4,672,969.

BACKGROUND OF THE INVENTION

This invention relates generally to method and apparatus for closing wounds and more particularly, to a method and apparatus for applying optical energy to biological tissue whereby the tissue is converted to a collagenous, denatured protein substance which joins severed tissues and closes wounds without injurious tissue shrinkage.

Various techniques have been used to repair wounds and closing surgical incisions including suturing, cryogenic, cauterization and tissue welding. Details of these techniques and their drawbacks are described in co-pending patent application Ser. No. 07/639,025, and U.S. Pat. Nos. 5,001,051, 4,854,320 and 4,672,969.

The preferred technique for tissue repair is laser welding. This technique is described in detail in co-pending patent application Ser. No. 07/639,025 and U.S. Pat. Nos. 5,001,051, 4,854,320 and 4,672,969 which are incorporated by reference. In laser welding, the tissue to be welded is heated to a predetermined temperature at which optical energy converts biological tissue into a collagenous substance. The collagenous substance contains bonds which can close closely approximated edges of tissue in a wound or lesion, together. The laser is controlled so that optical energy is converted into thermal energy bounded by a minimum absorption rate at which tissue is converted to a collagenous substance and a maximum absorption above which the water contained in the tissue wound boils.

A drawback to the aforementioned laser surgery technique is that when the laser converts the tissue to a collagenous substance and heated to a high enough temperature, the tissue begins to shrink. This shrinkage may result in disruptions in the bonds within the collagenous substance. A disruption in the bond has been determined to prevent tissue closure from occurring.

Another drawback is when the tissue is heated, a temperature gradient may form in the tissue. Consequently portions of the tissue become hotter than other portions resulting in tissue shrinkage of the hotter portions. Also when welding, the surgeon may position the laser incorrectly injuriously rewelding the area. These additional welding and absorption factors could overheat the tissue causing the tissue to coagulate and disrupt the start and subsequent efficacy of the closure.

SUMMARY OF THE INVENTION

This invention provides a method and apparatus for the controlled application of optical energy to convert biological tissue into a collagenous substance for facilitating healing and wound closure. In accordance with the invention, responsive to an input signal representative of a characteristic of the tissue for which closure is sought, the parameters of a generated beam of optical energy guided to the area of intended juncture are controlled and periodically excited to cause the amount of optical energy delivered to the tissue in the vicinity of the wound to be within a tissue nondestructive range. This range is selected to cause the tissue to be converted to a denatured proteinaceous substance which forms a biological glue that efficaciously closes the wound.

The intensity and uniformity of the optical energy is controlled such that the rate at which such optical energy is absorbed by the tissue in the vicinity of the wound and converted into thermal energy is within a tissue nondestructive range. This range is bounded by a minimum absorption rate at which the tissue denatures and a maximum absorption rate above which the tissue wound coagulates.

In accordance with the invention, a beam of optical energy is produced by a source, illustratively a laser, having a wavelength selected such that the optical energy from the laser is propagated without substantial attenuation through water and/or blood, but is absorbed in the biological tissue desired to be repaired. Such substantially unattenuated transmission through water and blood simplifies surgical procedures by obviating the need for operation in a dry, clean field. The arrangement is further provided with a guide, such as a flexible stainless steel wire, which provides for a predetermined distance for the beam of optical energy to the wound in the tissue. Moreover, the arrangement is provided with means for controlling the parameters of the beam so that the delivered energy is controlled to remain at a predetermined level. The energy level applied to the tissue is selected to convert the tissue in the vicinity of the wound to a collagenous substance. The energy level applied is selected to prevent the tissue being repaired from coagulating, injurious shrinking and thermal overheating.

In another embodiment of the invention, described in greater detail below, the optical energy source is constituted by a Nd:YAG laser which is tuned or is tunable to about 1.323 microns. Beam intensity control is provided by circuitry that regulates the laser power source. The flexible optical fiber is provided with a shutter and timer on a foot or hand-operated switch to regulate exposure time. The shutter is periodically cycled off and on to provide a controlled and homogenous rise in heat in the tissue being welded along the incision. The optical fiber is provided with a hand-piece that includes either a sliding scale or a fixed distance which sets beam spot size at the tissue by establishing the working distance between the beam emitting end of the hand-piece and the tissue being operated on. In response to input information on tissue type and thickness, a computer establishes the parameters for the beam intensity control circuitry, shutter timer and hand-piece scale required to achieve the proper energy level for tissue welding.

BRIEF DESCRIPTION OF THE DRAWINGS

Embodiments of the invention have been chosen for purposes of illustration and description, with reference to the accompanying drawings, wherein.

DESCRIPTION OF THE PREFERRED EMBODIMENTS

Biological tissue comprises cell layers in a protein framework for tensile strength. All proteins are amino acids which have side chains which are dissolvable either in water or fat. Naturation is a process wherein the amino acids fold over, always in the same configuration for each protein type, when the protein leaves the interior of a cell and is confronted with tissue water. In such case, the hydrophobic portion of a side chain folds to the interior of the molecule. The proteinaceous components of the tissue can be unfolded or denatured by the application of heat.

As stated in U.S. Pat. No. 4,672,969, it has been discovered that application of optical energy to biological tissue, in a nondestructive amount sufficient to generate enough heat to denature the proteinaceous components. Optical energy can be applied to the body's own tissues to substantially reproduce the prior tissue structure at a wound or severed tissue site without shrinking the tissue. In particular, energy from an optical energy source, such as a laser, can be applied in a periodic cycle to bring the temperature of biological tissue somewhere above room temperature, but below the point at which tissue coagulates; preferably above 45 degrees centigrade and particularly to below about 65 degrees centigrade. Collagen, a major source of protein in the body, is denatured by application of such energy in such a way as to go into solution and form a "biological glue" to seal a lesion, anastomize a severed vessel, or reconstruct damaged tissue. When the source of heat is removed the proteins begin to re-nature and form an approximate replication of the prior tissue structure. As the body heals, the so-called "biological glue" will be reabsorbed and replaced by natural tissue.

The application of heat in a periodic cycle to form a collagenous seal to immediately close a lesion or anastomize a severed vessel accelerates healing time, leaves little or no scarring, prevents tissue deterioration, preserves the tissue, and avoids inflammation and/or infection caused by the inclusion of foreign suture material in a wound.

Optical energy of a particular wavelength is converted to heat in tissue which absorbs energy at that wavelength. As detailed in U.S. Pat. No. 4,672,969, it was discovered that optical energy having a wavelength of about 1.2 to 1.4 micrometers is relatively unattenuated in both water and blood and, so, is particularly advantageous for use as an optical energy source for the formation of a "biological glue" in order to effect repair of gastrointestinal tract tissue, close skin wounds (whether originating accidentally, intentionally or through biological processes), and repair and reconstruct tissue such as reproductive tissue, tendons, and vascular tissue, provided the intensity, exposure time and spot size of the beam at its point of incidence on the tissue are controlled to keep the energy absorption by the tissue within the desirable range. A suitable wavelength is obtainable using a commercially available Nd:YAG laser configured to generate optical energy at a wavelength of about 1.32 micrometers.

Figure 1:
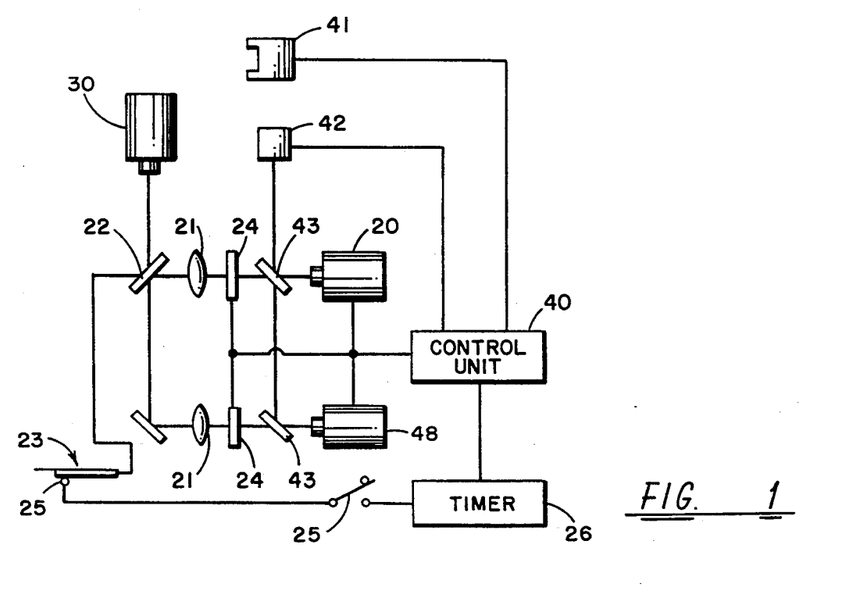
FIG. 1 is a schematic view of a laser surgical system for use in accordance with the invention.

FIG. 1 illustrates a surgical system for achieving tissue welding in accordance with the invention. The system has a source of optical energy, laser 20, which is preferably of the Nd:YAG crystalline variety wherein an yttrium-aluminum-garnet(YAG) rod is doped with neodymium (Nd) ions as the active light-producing element. Such a laser 20 includes a resonant cavity for amplifying the emitted light and pumping means, such as a DC Krypton arc lamp or diode, for supplying energy to create a population inversion of the normal energy state of Nd ions. The population inversion results in the stimulated emission of light according to well-known laser principles.

Absent any tuning of the laser cavity, Nd:YAG lasers will emit light at a fundamental dominant wavelength of 1.06 micrometers. Such lasers also emit light at a secondary wavelength of approximately 1.322 micrometers. Proper utilization of this secondary mode in laser operation requires the dominant emission, which has a greater amplitude than the secondary emission, to be suppressed. Typically, peak power output at this secondary emission level is 20–30% of the continuous wave peak power output dominant level. It is the secondary wavelength that is utilized in the method and apparatus of the invention.

As readily understood by persons skilled in the art, laser 20 includes a power supply circuit for activating the pumping arc lamp and cooling means for cooling the laser. A suitable Nd:YAG laser for use in this invention is produced by PROCLOSURE INC., Orlando, Fla. 32809.

A lens 21 is provided to focus the emerging coherent light beam from laser 20 into an optical fiber 22. Lens 21 may comprise a system of lenses. Optical fiber 22 efficiently transmits the desired wavelength. Optical fiber 22 provides a flexible conduit for guiding the optical energy from the laser into a hand-piece or wand 23 which is manipulable by the physician. A shutter 24 is located, preferably, between laser 20 and lens 21. Hand-piece 23 contains a shutter switch 25 which is preferably a foot switch that controls release of the laser energy and which may be actuated by either the hand or the foot of the operator. A timer 26 is provided to control the shutter cycle and duration, and, thereby, the energy exposure of the tissue to the laser. Hand-piece 23 may include a lens (not shown) for focusing or defocusing the beam.

Figures 2, 6:
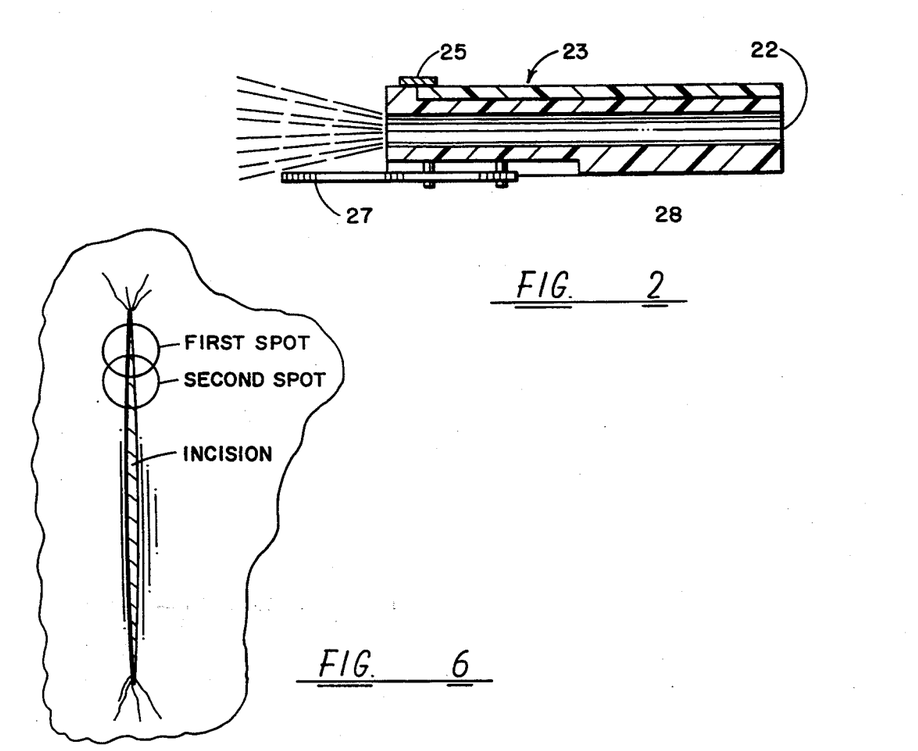
FIG. 2 is a side sectional view of the hand-piece of FIG. 1.
FIG. 6 is a top view of tissue being welded illustrating placement of a laser spot in accordance with the invention.

Advantageously, hand-piece 23 includes means to enable the physician to set the working distance between the tissue to be irradiated and the distalmost end of the optical fiber or lens. In an illustrative embodiment, as shown in FIG. 2, a sliding scale 27 (or fixed scale) which cooperates with a protective case 28 on the end of optical fiber 22 controls the working distance, and hence the diameter of the beam spot. As shown in FIG. 2, the divergence of the beam is used to control the beam diameter as the distance between the distalmost end of the fiber 22 and the tissue is increased or decreased.

For a given suitable optical wavelength and mode or beam geometry, the following electro-optical parameters require proper adjustment for each type of tissue: output power, time exposure, duration between exposure, and beam spot size. In particular, the thermal effects on the tissue can be controlled by proper selection of the electro-optical parameters. Power density measures the energy concentration of the applied light beam and is typically expressed in watts per square centimeter area of the applied beam spot. Power density is directly related to the amount of heat that will be produced at a given absorptivity. Radiant exposure, expressed in joules per square centimeter, is a measure of the power density multiplied by the exposure time. If the wavelength of the applied beam is poorly absorbed, more heat can be generated by increasing the time of tissue exposure to the applied beam. Laser output power and beam spot size selections affect the power density; overall radiant exposure is affected by power density, time exposure and duration between exposures selections.

Suitable means for control of the power output of laser 20 is provided by a control unit 40, described further with reference to FIG. 3, below. Optical output power detector 41 is provided for initial calibration of the beam of laser 20 at start-up and a second detector 42, which always receives a portion of the beam of laser 20 output. The power delivered to the tissue surface should be maintained under 2 watts for a 1–3 mm distance between the tip of a 0.400μ diameter fiber and the tissue for purposes of tissue reconstruction by laser 20 as described herein. The object is to deliver a specific amount of energy per volume of tissue. For a given spot size, which is related to the volume of tissue exposed, there are many combinations of power output and time exposure which will deliver equivalent amounts of energy. To-wit, power delivered to the tissue typically ranges between 0.5 and 2 watts; although power delivered could go higher if the time exposure were reduced commensurately.

In the lowest order transmission mode, $TEM_{00}$ specifically, a more concentrated beam results which can be used for cutting purposes at higher power output or for achieving very small beam spot size for tissue reconstruction. In the alternative, multimode transmission can be used for tissue reconstruction, but the beam spot size can not be as finely focused as the $TEM_{00}$ mode. However, if the beam is defocused, less power is delivered per unit area.

Laser parameters for other tissue types being evaluated, as well as modifications to the laser parameters in this application will be determinable from the herein disclosed information without extensive or undue experimentation.

In a particularly advantageous embodiment, data relating to appropriate settings of electro-optical parameters for various tissue types can be coded on a computer memory device, such as floppy disc or programmable read-only memory computer chip. The functions of control unit 40 and timer 26 can be computer controlled to adjust automatically the power level, and time exposure, duration between exposures, and display the proper spot size upon input of tissue type and the operating conditions by the physician or surgeon.

The system of FIG. 1 also includes a marker laser 30, illustratively a low-power helium-neon laser, which is coaligned with the infrared beam of laser 20. Laser 30, however, can be of any type which emits radiation in the visible range of the electromagnetic spectrum. The power rating of the helium-neon marker laser 30 is preferably between 0.5–5 mWatts. Marker laser 30 can be arranged so that its focal point coincides with that of the main operating laser 20.

Figure 3:
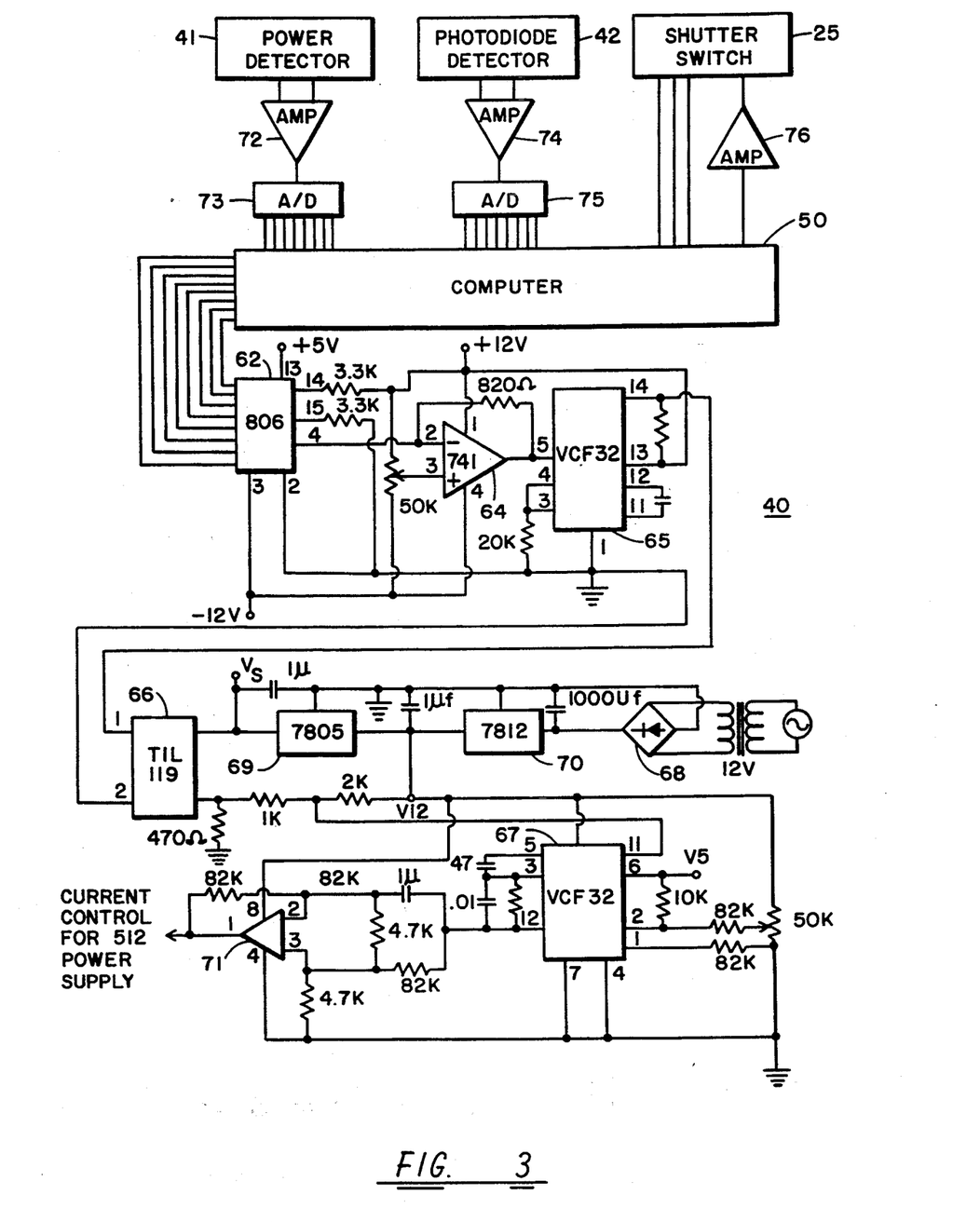
FIG. 3 is a block and schematic diagram of microprocessor control circuitry usable in the system of FIG. 1.

FIG. 3 shows suitable circuitry for implementation of the functions of the control unit 40 and timer 26 which utilizes a microprocessor or computer 50, such as provided in a conventional personal computer, for controlling parameters of the optical beam so as to deliver the appropriate amount of energy to the tissue reconstruction site. In response to input by the physician of the applicable tissue type and thickness, the computer 50 accesses a data base stored in a memory device to establish appropriate settings for power level, time exposure, duration between exposures, and spot size.

Optical output power is controlled by delivery of a signal from the microprocessor to the conventional current control circuitry for the power supply of the laser 20. A digital-to-analog converter 62 is connected to receive a digital current control signal from the microprocessor 50. The analog output of the converter 62 is amplified by an amplifier 64 and then converted to a frequency signal by a voltage-to-frequency converter 65. The output of the converter 65 is used via an isolating circuit 66 to drive a frequency-to-voltage converter 67 to deliver a signal from a power source 68 and voltage regulators 69, 70 through an amplifier 71 to the power control input of the laser 20. The isolation between the computer 50 and the laser 20 is provided for protective purposes and may be achieved through use of an optocoupler.

Verification of power setting accuracy is accomplished initially by requiring that the wand 23 end of the optical fiber 22 be inserted in the calibration port of power detector 41 located in a system console (not shown).

The power detector 41 may take the form of a coherent power detector, such as a thermal calorimeter. Following determination by the computer 50 of the correct power setting for the laser 20 for a particular tissue type and thickness, at first fire-up of the lamp the hand-piece or wand 23 is inserted in a receptacle on the control unit console. Continuous firing of the laser is prevented unless the hand-piece 23 is in the receptacle.

The output of the detector 41 is amplified by an amplifier 72 and converted in an analog-to-digital converter 73 for input to the computer 50. The computer 50 then performs a calibration subroutine to adjust the digital output to the converter 62 and thus to the laser power source, until the desired optical power output is read at the power detector 41. If the intensity of the beam output is too low, the value of the digital signal to converter 62 is incremented; if the output is too high, it is decremented. The computer 50 will then clear the system for operation outside of the receptacle under control of the shutter switches 25 and timer 26. Subsequent beam output adjustment is undertaken by computer 50, in accordance with well-known principles, by which a small amount of the optical output is diverted by the beam splitter 43 (FIG. 1) for measurement by the detector 42, which suitably takes the form of a photodiode connected through an amplifier 74 and an analog-to-digital converter 75 to deliver a power level input to the computer 50. The photodiode 42 circuit provides a continuous feedback loop through the computer 50 for power output verification.

Figure 5A:
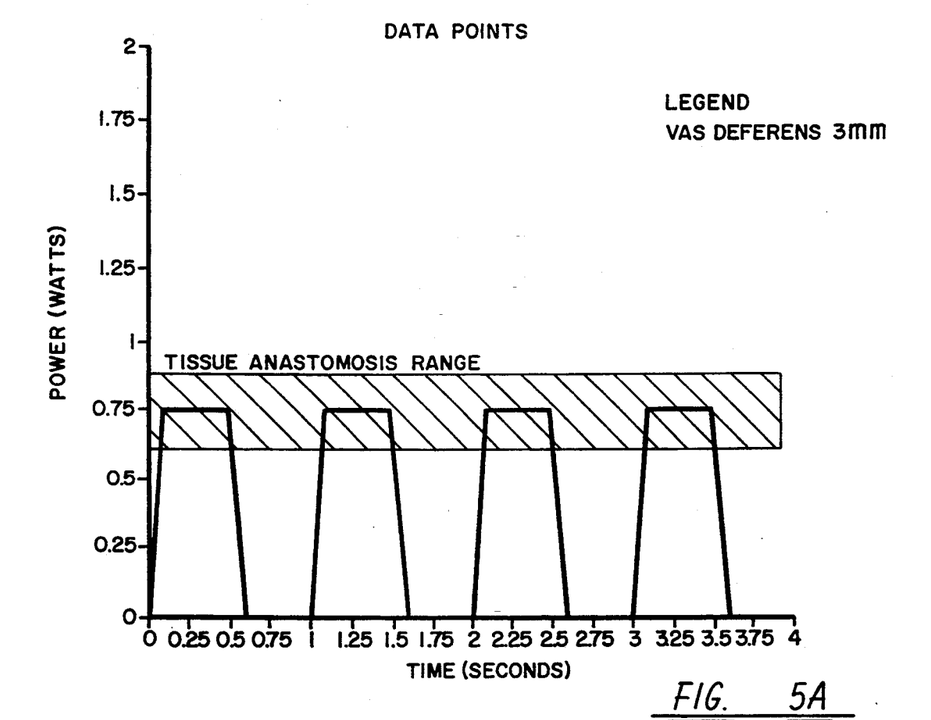
FIGS. 5A–5F are examples of heating curves for closing wounds on various types of tissue.
Figure 5B:
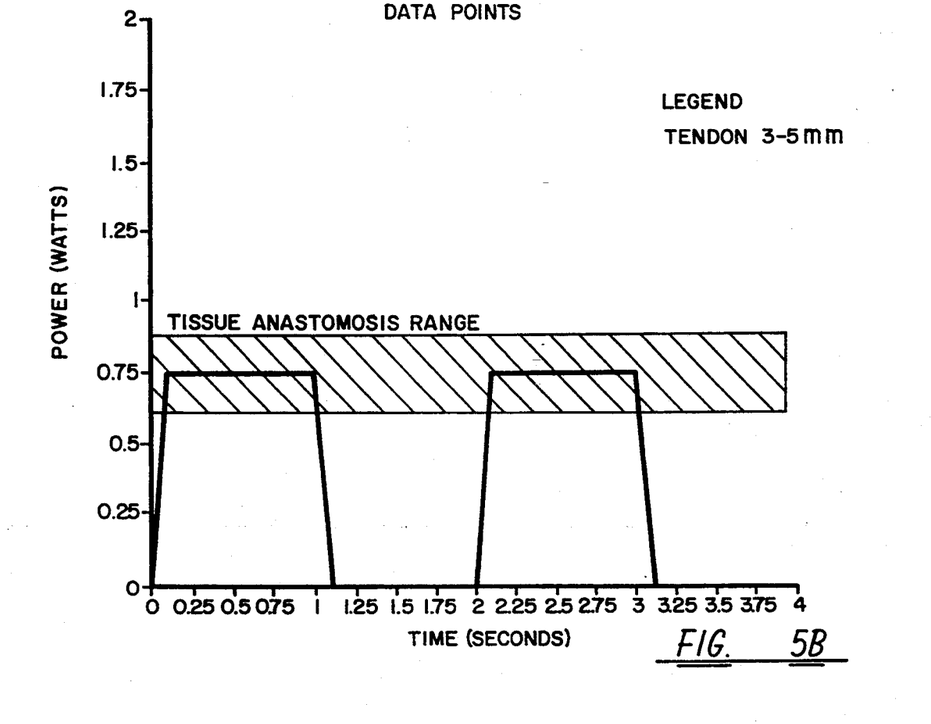
Figure 5C:
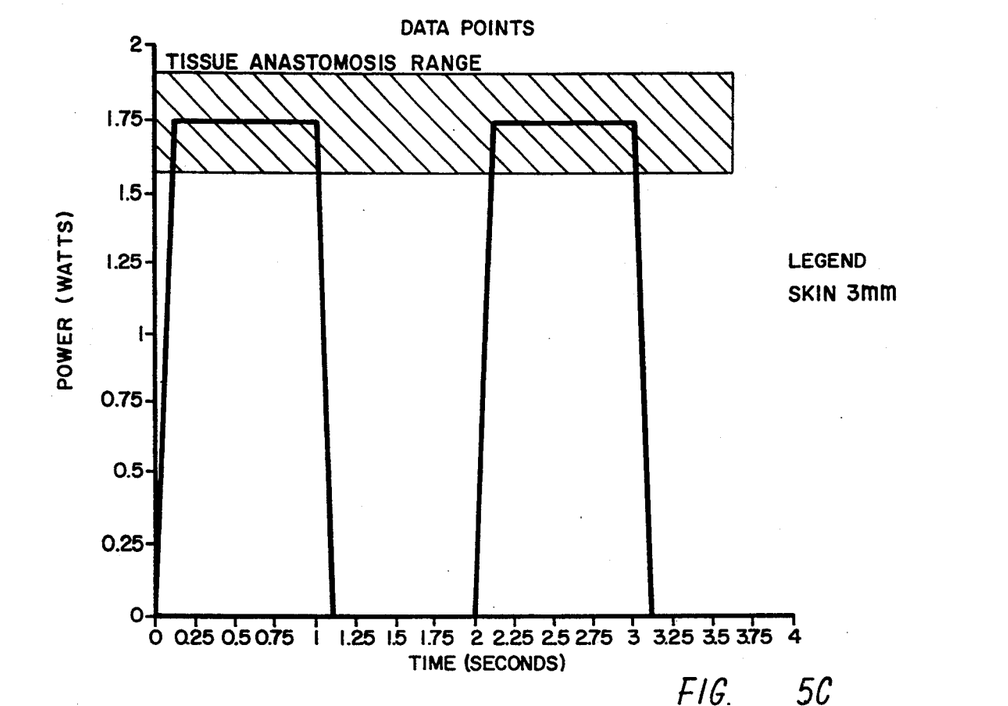
Figure 5D:
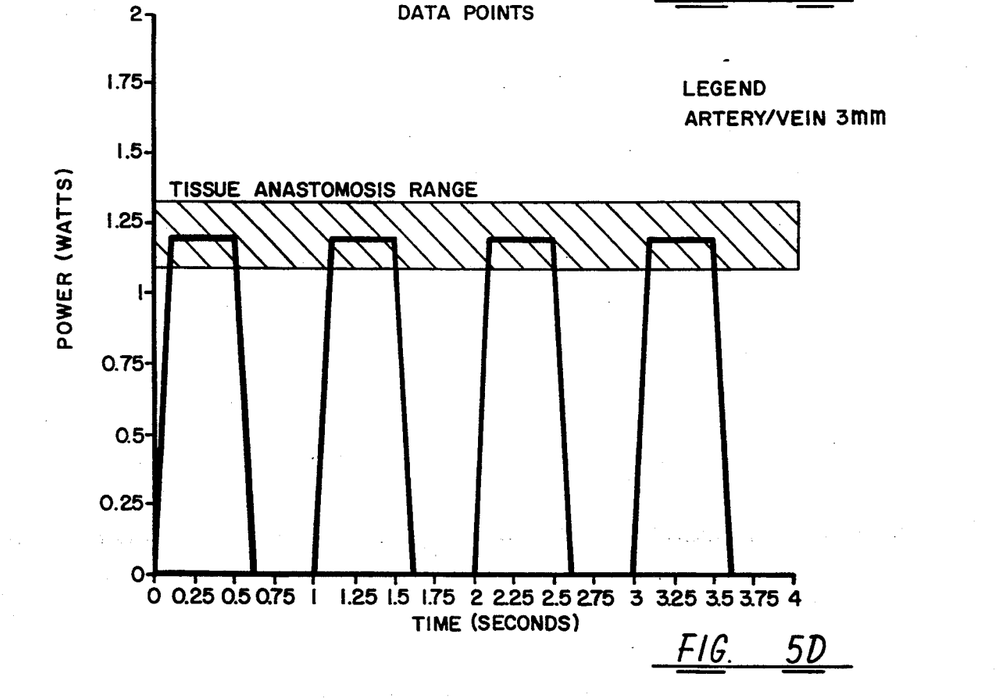
Figure 5E:
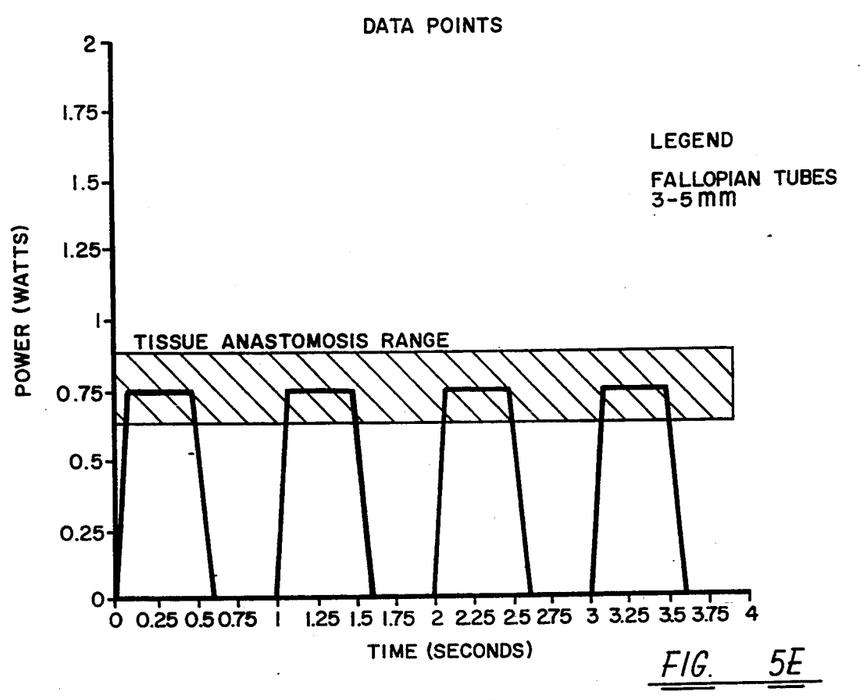
Figure 5F:
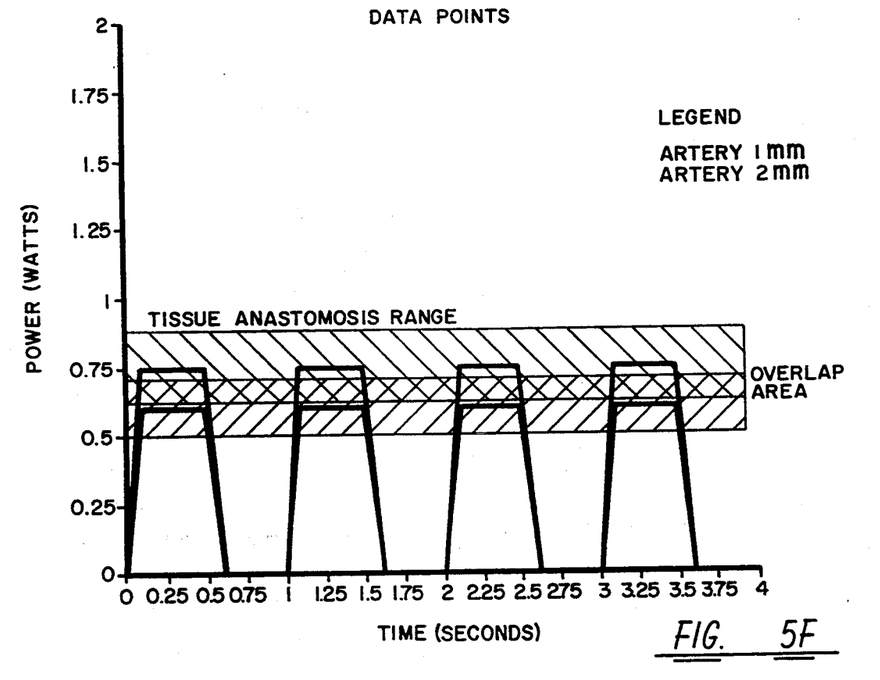

As already indicated, a shutter switch 25 (FIG. 1) is provided control to emissions of the beam toward the tissue. For control of the total energy applied, the computer 50 also serves the function of a timer 26 (FIG. 1) to limit the total time for which shutter 24 permits the beam from laser 20 to reach the tissue on any one shot. Computer 50 also sets the duration between exposures. The shutter 24 is arranged to normally be in a beam blocking position. The switch 25 is connected to the computer 50 with the aid of an amplifier 76, as shown in FIG. 3, and programming is provided so that a counter is set up to increment for each clock pulse received during the time that shutter 24 is open. When the count indicates that the total specified exposure time set by computer 50 is reached, the shutter will be closed and blocked from reopening until a predetermined time delay has passed. The exact exposure time and time delays are explained in more detail in FIGS. 5A–5C. By setting delay and exposure time, it is ensured that each passage of beam energy from the laser 20 will have the required energy to denature tissue without coagulation. Cycling the tissue exposure in this manner permits the user to overlap welds without overheating the tissue. It will be appreciated that other arrangements for the timer 26 and shutter control circuitry are possible and that, in particular, the function by programming in computer 50 can be replaced by hardwired timer circuitry, if desired.

For the illustrated embodiment, the diameter or the beam spot at the point of impact with the tissue is controlled by setting the working distance from the distal-most end of the fiber 22 to the tissue. As shown in FIG. 2, this is accomplished by manual manipulation of the sliding scale 27 (or fixed scale) or probe to achieve the distance specified by the computer 50 to give the required beam diameter and beam energy density required for the subject tissue type and thickness. In response to input of the tissue characteristics, the computer displays the required setting. It will be appreciated that beam shaping may be accomplished in other ways and that the scale movement can be accomplished automatically, if desired. The shown means is, however, a simple workable approach that lends itself readily and inexpensively for use on a disposable optical fiber 22 for use in a sterile environment.

For input of tissue characteristics to the computer 50 a conventional data input device, such as a keyboard is used. Known touch screen or voice activated input devices may also be used. It is preferable for the input process to be undertaken under prompting by tissue type and thickness selection menus appearing on a visual display.

Figure 4A:
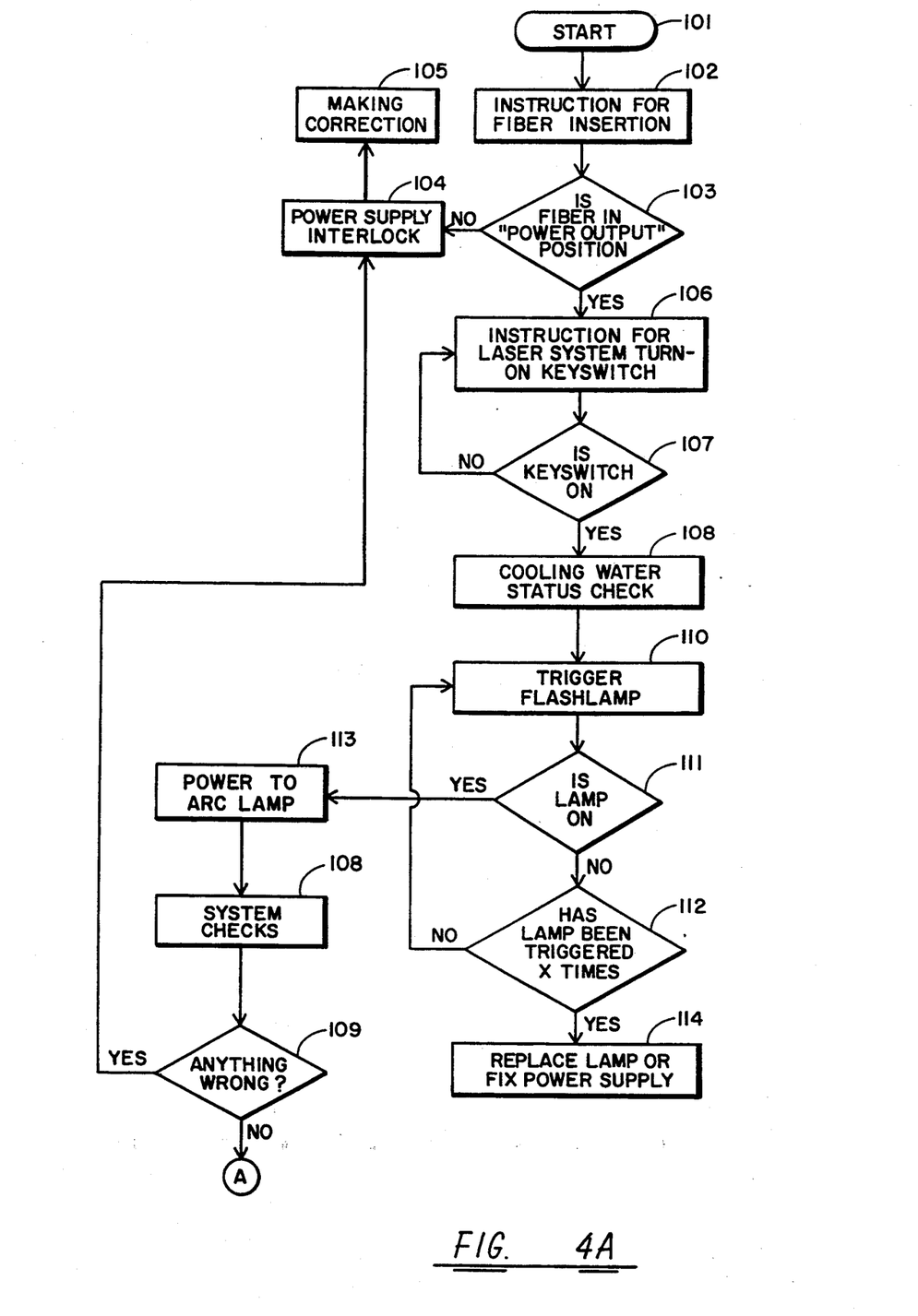
FIG. 4A, 4B and 4C are flow diagrams of software programs for use by the microprocessor of FIG. 3.
Figure 4B:
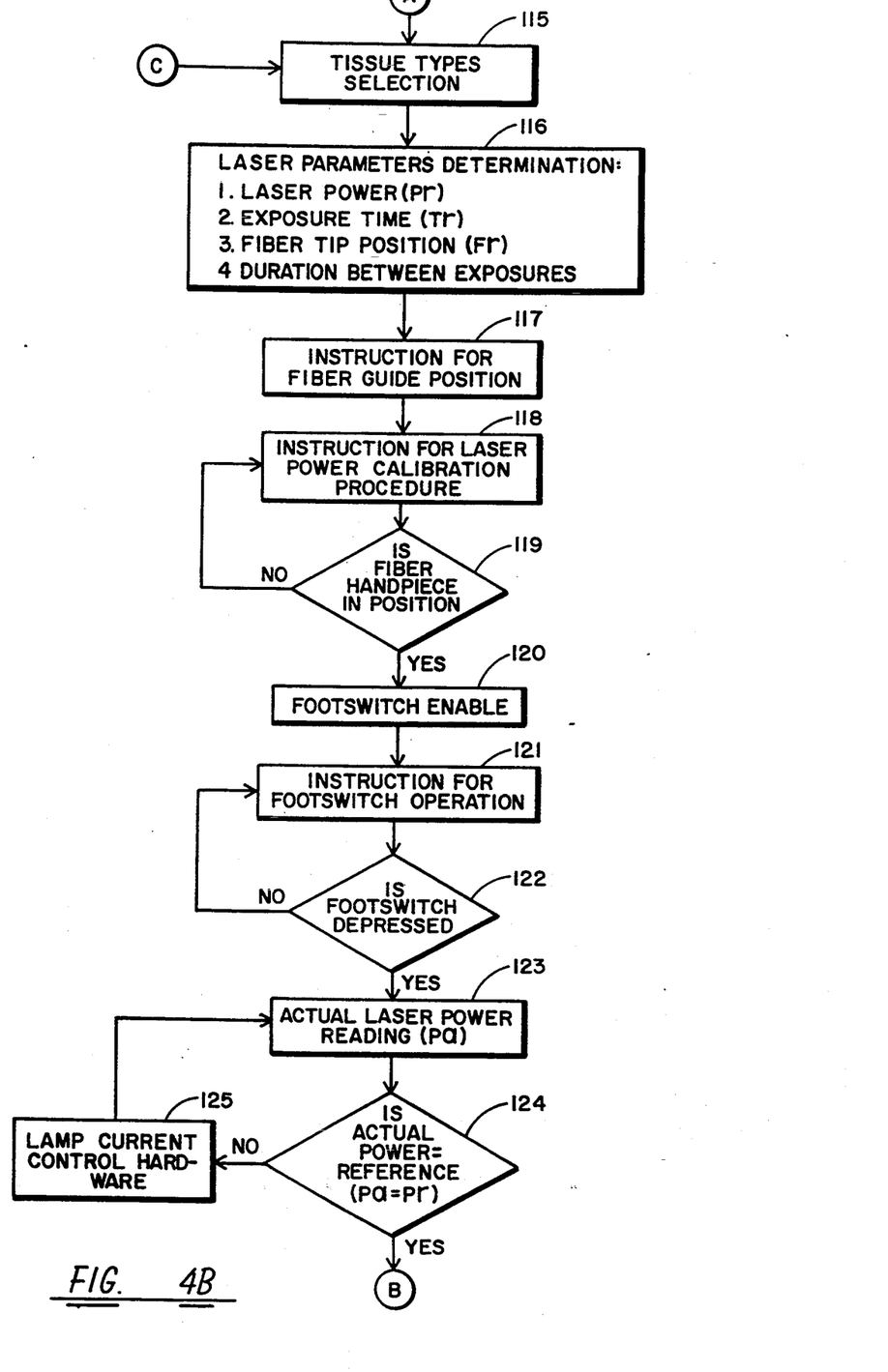
Figure 4C:
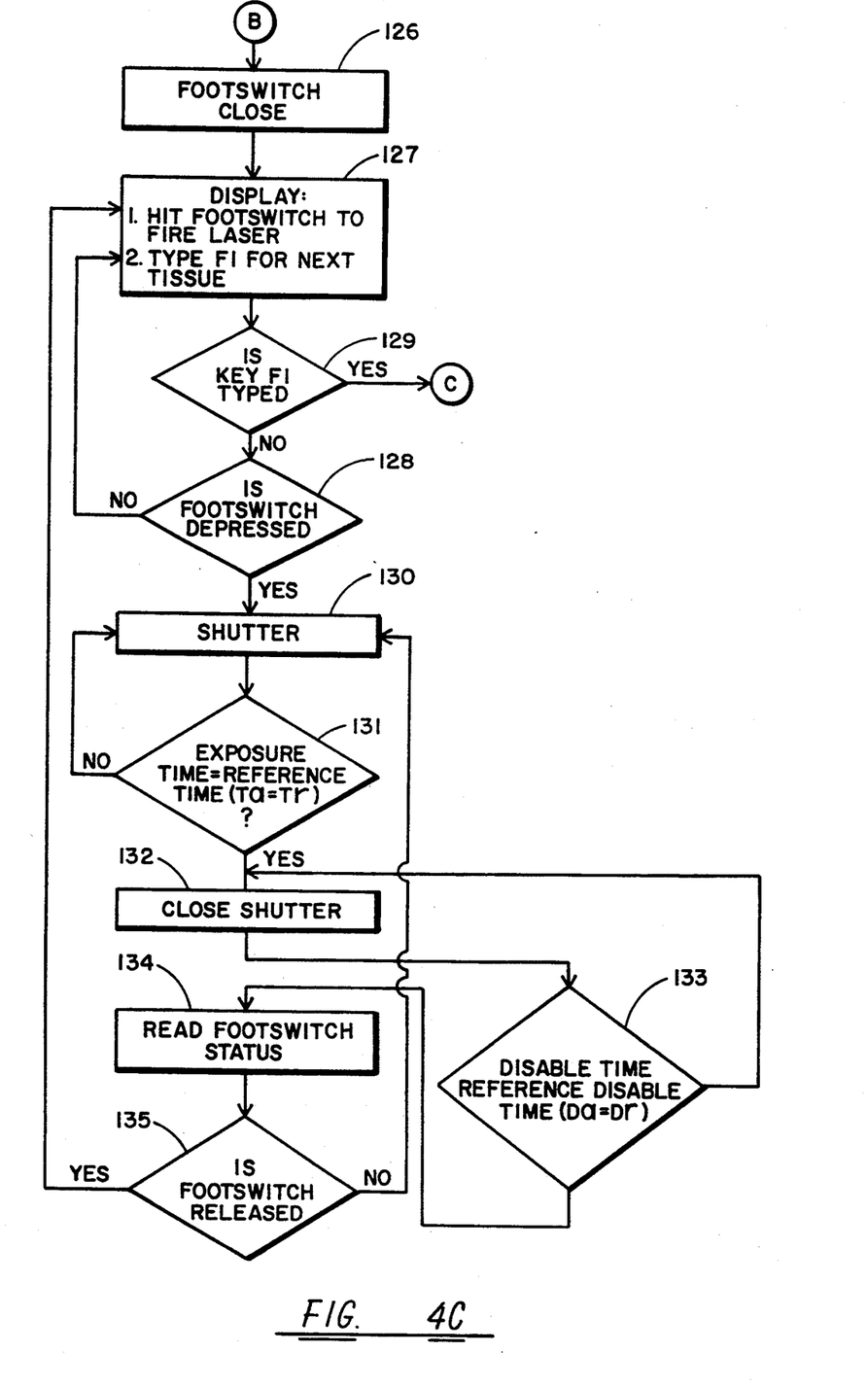

FIGS. 4A–4C present an overall flow diagram of the software steps performed by the computer 50 for controlling the parameters of the beam in accordance with selected tissue characteristics. As a first step in readying the system for use, the computer 50 undergoes a series of checks. At the start 101 of the program, instructions are given at 102 on a display device, such as a cathode ray tube screen, for insertion of nonwand end of the fiber into the laser console. In order to engage the laser power supply, the fiber has to be in the inserted "power output" ready position. If the fiber is not in the correct position the power supply to the system will be disabled at 103, 104, preventing operation of the laser 20 until a correction is made at 105. Optionally steps 102, 103 and 106 can be eliminated if the fiber 22 is built into the laser system.

The illustrated embodiment contemplates the use of a key switch on the operating console, so the laser system awaits the positioning of that switch to the on position before proceeding. Upon receipt at 107 of the awaited keyswitch signal, the program then proceeds, at 110, the program initiates a signal to fire the krypton lamp to activate the laser 20. A determination is made, such as by looking at the signal from detector 42 (FIG. 3) at 111 to ensure that the lamp is on. If the lamp is not on, retriggering is initiated at 112. If after a predetermined number (x) attempts, the lamp does not light, a message is displayed at 114 to replace the lamp or repair the power supply. This predetermined number x, is adjustable and can be set by the user.

If the flashlamp does light, at 113, the arc lamp is lit. The program then proceeds to do some preliminary checks, such as checking the status of the laser cooling system at 108. For example, the deionized water is checked for proper conductivity, pressure and temperature. Other checks and diagnostics can also be run. Also, security subroutines can be implemented at this or another stage to ensure that only authorized individuals operate the beam itself. Should the diagnostics or other checks indicate some discrepancy at 109, the program will be directed to block further operation of the system, as at 104. If everything checks out the program then moves to an input requesting posture to define the beam according to the tissue to which it will be applied. At 115, tissue characteristics are entered into the computer 50. A suitable way to accomplish that is to utilize a menu-driven tissue selection process. Available tissue selections are displayed on the screen, and input is solicited. Once tissue type is entered, the menu will be changed to solicit input as to tissue thickness. When the tissue thickness has been selected, the computer 50 addresses data stored in a memory device, such as a disk in a disk drive, and at 116 determines the laser operation parameters appropriate for the selected tissue characteristics.

It is advisable to provide some feedback to the user on tissue type and thickness to guard against input error. This can be done using any of several well known techniques. One way is to display graphic representations of the selected tissue type and thickness on a display screen to provide an easily identifiable visual check to give reassurance to the user.

For the embodiment described, the laser parameters obtained from lookup in the memory storage device include a combination of laser power (Pr), exposure time (Tr), duration between exposures (Dr) and fiber tip position (Fr) settings that will deliver a controlled amount of optical energy to the selected tissue type and thickness to nondestructively convert it to a denatured proteinaceous collagenous substance to close or join it together without injuriously shrinking the tissue.

The laser power and exposure time parameters are fed to assembly programs for direct control of the power and shutter control circuitry described previously. For manual adjustment of the beam spot diameter in the manner contemplated by the described embodiment, instructions for manual setting of the fiber guide sliding scale 27 to establish the correct fiber tip position (Fr) are displayed on the screen at 117. Preferably a handpiece with fiber guide, such as a flexible stainless steel wire having a fixed length (Fr) is used. When another distance (Fr) is required, a handpiece with a guide having a different length is selected.

Once the parameters are determined and the distance guide 27 set, instructions are displayed at 118 for initial calibration of the beam. At 119, the program checks to ensure that the fiber hand-piece 23 is properly inserted into the receptacle part of the power detector 41 (FIG. 3). For safety reasons, if the fiber hand-piece is not in the sensor position at this stage, the program loops back to 118. Switch 25 is enabled at 120 to permit operation of the shutter 24 for initial calibration. Instructions for footswitch (handswitch) operation are given at 121.

Shutter switch 25 actuation is monitored at 122. At 123–125, the actual laser beam output reading (Pa) detected by the detector 41 (FIG. 3) is compared with the computer 50 designated reference output Pr. The lamp current control hardware is adjusted until the measured output power is the same as the computer specified output power. The switch 25 is then closed at 126. The shutter 24 will close as soon as Pa=Pr is established. Once initial calibration over, the laser is set for tissue use.

Through menu selection choice or other input procedure as shown at 127, the user can proceed to control the shutter 24 with the switch 25 at 128 in order to conduct the tissue joining process. Alternatively, the user can elect at 129 to revise the parameters to those more suited to another tissue, whereupon the program will repeat the previous steps.

Depressing the switch 25 will open the shutter 24 for tissue welding at 130. The shutter open time will be monitored as already described, with the shutter 24 closing when the timed actual exposure time Ta reaches the specified exposure time Tr, at 131. When the Ta=Tr, the shutter is closed at 132 and a disable time tissue at the lesion site is heated to a temperature sufficient to cause denaturization of the tissue proteins to the depth necessary to reconstruct the tissue in the lesion irrespective of whether the operating field is bloody or wet. The electro-optical parameters are set and controlled in response to input as to tissue type and thickness. Parameters may be specified for the reconstruction of many soft tissues such as; vascular, skin,, tendon, vas deferens, fallopian tubes, gastrointestinal tract, dura, and sclera. With an appropriately controlled moldification of the level of power delivered to the tissue under repair, cartilage and tympanic membranes can also be repaired in accordance with the invention described hereinabove.

Referring to FIG. 5A–5F, there is shown exemplary heating curves for various tissue types. The tissue and laser parameters for these curves are summarized in the following Table I. These parameters are by no means all exclusive; it is envisioned that other parameters can be used with modifications and it is intended that this table be exemplary of a preferred embodiment only.

TABLE I

LASER PARAMETERS FOR VARIOUS TISSUE TYPES

| Tissue | Tissue Thickness In Millimeters | Probe Distance | Spot Size Diameter (with 400μ fiber) | Range Of Power (in Watts) | Exposure Duration On (Tr)/Off (Dr) | Approximate Tissue Final Energy Transferred J/CM$^2$ |
|---|---|---|---|---|---|---|
| Artery | 1 | 1 mm | .575–.646 mm | .5–.7 | 0.5 sec/0.5 sec | 4.63 |
| Artery | 2 | 1 mm | .575–.646 mm | .65–.85 | 0.5 sec/0.5 sec | 5.79 |
| Artery/Vein | 3 | 1 mm | .575–.646 mm | 1.1–1.3 | 0.5 sec/0.5 sec | 9.26 |
| Fallopian Tube | 3 | 1 mm | .575–.646 mm | .65–.85 | 0.5 sec/0.5 sec | 5.79 |
| Fallopian Tube | 4 | 1 mm | .575–.646 mm | .65–.85 | 0.5 sec/0.5 sec | 5.79 |
| Fallopian Tube | 5 | 1 mm | .575–.646 mm | .65–.85 | 0.5 sec/0.5 sec | 5.79 |
| Skin | 3 | 3 mm | .925–1.14 mm | 1.65–1.85 | 1.0 sec/1.0 sec | 13.31 |
| Vas Deferens | 3 | 1 mm | .574–646 mm | .65–.85 | 0.5 sec/0.5 sec | 5.79 |
| Tendon | 3 | 3 mm | .925–1.14 mm | .65–.85 | 1.0 sec/1.0 sec | 5.7 |
| Tendon | 4 | 3 mm | .925–1.14 mm | .65–.85 | 1.0 sec/1.0 sec | 5.7 |
| Tendon | 5 | 3 mm | .925–1.14 mm | .65–.85 | 1.0 sec/1.0 sec | 5.7 |

(Da) clock is started. When the computer reference shutter duration time is reached (Da=Dr) in 133, the footswitch status (depressed or released) is determined at 134. When the footswitch is released in 135, the timer is reset and the program directed back to step 127 to ready the system for another shot.

The program can be modified and embellished to meet specific needs. It can be integrated with a program to display patient case history data and to update the patient file automatically to record the details of the procedure applied to that patient.

In an illustrative embodiment, the apparatus of FIG. 1 is used for skin closure at a lesion site. The tissue edges of the lesion are brought into close approximation by manual manipulation, for example. Hand-piece 23 is positioned above the lesion at such a distance as to produce the desired beam spot size. Typically a 400μ diameter fiber is used, which has been found to have a total dispersion angle of about 12.0°±2°. Thus the diameter at the spot is determined to be 400μ+2 d tan (6.0°±1°), where d is the distance between the fiber tip and the tissue. The power, time exposure and spot size are set so as to heat the tissue above 45 degrees centigrade, but below the temperature at which tissue coagulates (typically 64°–65° C.). Typical spot sizes range from 0.57 mm to 1.2 mm for levels of power delivered to the tissue ranging from 0.5 to 2 watts, and time durations (Dr and Tr) range from about 0.5 to 1.0 seconds.

When the optical energy of laser 20 at 1.32 micrometers is released on the lesion site, with the electro-optical parameters adjusted as hereinabove suggested, the It is recognized by the inventors that by welding tissue using the aforementioned parameters, or by welding the aforementioned tissue while monitoring the energy delivered to the tissue using the approximate temperature parameters (<65° C.) in Table I, tissue is denatured without coagulating. Thus closely approximated ends of a lesion of tissue can be welded without shrinkage.

Referring to FIG. 6, there is shown spot placement using an exemplary technique of closing closely approximated edges of tissue. In this exemplary technique closely approximated edges along an incision line are placed adjacent each other. Probe 27 is positioned adjacent the tissue to be welded and the foot pedal is depressed to weld a first spot. While the foot pedal is depressed, the probe 27 is then positioned adjacent to the next spot along the incision line, to a second spot that overlaps the first spot. The user continues to weld in this manner until the incision is completely sealed. By cycling the duration and exposure of the laser when welding, the tissue can be continuously welded along the incision line by overlapping exposures and spot. When tissue is welded in this manner, the tissue remains at a denaturing temperature while preventing coagulation and shrinkage. Due to preselected (on/off) exposure cycle times repeatedly exposing the same spot to optical energy from hand piece 23 will not injure the tissue or negate the efficacy of closure.

The above-described embodiments are provided for the purpose of illustration and are not to be construed as limiting. Other modifications and adaptations can be made by those of skill in the art without departing from the spirit and scope of the invention. In particular, the laser energy can be transmitted to the patient treatment site by an articulated arm with mirrors or it can be transmitted to the interior of a patient by endoscope. Moreover, materials other than neodymium-doped crystalline yttrium-aluminum-garnet can be used as a lasing medium to generate optical energy at the desired wavelengths.

What is claimed is:

1. A method of reconstructing biological tissue wherein a proteinaceous framework is formed from denatured protein in a vicinity of tissue being reconstructed, the proteinaceous framework approximates the tissue being reconstructed, the method comprising the steps of:

providing a source of optical energy which is capable of treating the biological tissue; and non-destructively applying optical energy in a periodic cycle to the biological tissue at such wavelength and at such power dissipation as to cause an amount of optical energy to be absorbed and to be converted to heat such that the energy absorbed and converted to heat within substantially all of the tissue being reconstructed is within a range bounded by a minimum absorption rate at which tissue denatures and a maximum absorption rate at which the tissue coagulates, such that proteinaceous elements of the biological tissue denatures without the biological tissue shrinking.

2. The method as recited in claim 1 wherein said wavelength is in the range of about 1.2 to 1.4 micrometers.

3. The method as recited in claim 1 wherein said tissue being reconstructed is an artery having a tissue thickness of about 1–3 mm, and wherein the amount of optical energy described in the tissue is about 4–10 J/CM$^2$.

4. The method as recited in claim 3 wherein said energy is non-destructively applied to said artery having about 0.5–0.7 watts of power with a 0.5 second on duration and a 0.5 second off duration.

5. The method as recited in claim 1 wherein said tissue being reconstructed is skin having a tissue thickness of about 3 mm, and wherein the amount of optical energy absorbed of the tissue is about 13.3 J/CM$^2$.

6. The method as recited in claim 5 wherein said energy is non-destructively applied to said skin having about 1.6–1.9 watts of power with a 1 second on duration and a 1 second off duration.

7. The method as recited in claim 1 wherein said tissue being reconstructed is a Fallopian tube having a tissue thickness of about 1 mm, and wherein the amount of optical energy absorbed in the tissue is about 5.79 J/CM$^2$.

8. The method as recited in claim 7 wherein said energy is non-destructively applied to said Fallopian tube having about 0.6–0.9 watts of power with a 0.5 second on duration and a 0.5 second off duration.

9. The method as recited in claim 1 wherein said tissue being reconstructed is a vas deferens having a tissue thickness about 3 mm, and wherein the amount of optical energy absorbed in the tissue is about 5.8 J/CM$^2$.

10. The method as recited in claim 9 wherein said energy is non-destructively applied to said vas deferens having about 0.6–0.9 watts of power with a 0.5 second on duration and a 0.5 second off duration.

11. The method as recited in claim 1 wherein said tissue being reconstructed is a tendon having a tissue thickness of about 3–5 mm, and wherein the amount of optical energy absorbed in the tendon is about 5.7 J/CM$^2$.

12. The method as recited in claim 11 wherein said energy is non-destructively applied to said tendon having about 0.6–0.9 watts of power with a 1 second on duration and a 1 second off duration.

13. The method as recited in claim 1, further comprising the steps of:

applying a spot of optical energy at a first location at the wavelength onto the tissue to be reconstructed for sufficient duration and energy to denature the tissue under the spot without coagulating the tissue;

disabling the optical energy applied to the spot for a duration bounded by a maximum value at which a temperature of the tissue falls below a tissue denature temperature;

moving the location of the spot to a second spot location along an incision;

enabling the optical energy at the second location so that a portion of the spot at the second location overlaps a portion of the spot at the first location; and applying the optical energy on the second spot at the wavelength for sufficient duration and energy to denature the tissue under the second spot location without coagulating the tissue.

14. An apparatus for reconstruction biological tissue to form a proteinaceous framework from denatured protein where the proteinaceous framework approximates the tissue being reconstructed, the apparatus comprises:

a source of optical energy which is capable of heating biological tissue; and means for maintaining the optical energy from the source when heating biological tissue at such wavelength and such power dissipation as to cause an amount of optical energy to be absorbed and to be converted to heat such that substantially all of the tissue being reconstructed falls within a range bounded by a minimum absorption rate at which tissue denatures and a maximum absorption rate at which tissue coagulates to allow proteinaceous elements of the biological tissue to denature without the tissue shrinking.

15. The apparatus as recited in claim 14 wherein said source of optical energy is provided at a wavelength in the range of about 1.2 to 1.4 micrometers.

16. The apparatus as recited in claim 14 further comprising:

means for inputting a tissue type; and means for maintaining the range of optical energy applied at a power level between about 0.5 and 2 watts for a tissue spot size of between about 0.5 and 1.4 mm diameter.

* * * * *